United States Patent
Sirinyan et al.

(10) Patent No.: US 9,609,871 B2
(45) Date of Patent: *Apr. 4, 2017

(54) COMBINATION PRODUCT FOR CONTROLLING PARASITES ON ANIMALS

(71) Applicant: Bayer Animal Health GmbH, Leverkusen (DE)

(72) Inventors: Kirkor Sirinyan, Bergisch Gladbach (DE); Andreas Turberg, Haan (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/862,103

(22) Filed: Sep. 22, 2015

(65) Prior Publication Data

US 2016/0007611 A1 Jan. 14, 2016

Related U.S. Application Data

(63) Continuation of application No. 13/282,588, filed on Oct. 27, 2011, now Pat. No. 9,137,995, which is a continuation of application No. 12/520,552, filed on Jul. 7, 2009, now Pat. No. 8,071,116.

(51) Int. Cl.
| | | |
|---|---|---|
| *A01N 53/00* | (2006.01) |
| *A01N 43/56* | (2006.01) |
| *A01N 47/02* | (2006.01) |
| *A61K 31/415* | (2006.01) |

(52) U.S. Cl.
CPC ............ *A01N 53/00* (2013.01); *A01N 43/56* (2013.01); *A01N 47/02* (2013.01); *A61K 31/415* (2013.01)

(58) Field of Classification Search
CPC .... A01N 2300/00; A01N 53/00; A01N 43/56; A01N 47/02; A01N 25/02; A01N 43/28; A01N 47/48; A01N 25/30; A01N 43/90; A01N 47/38; A01N 57/16; A01N 31/14; A01N 43/88; A01N 51/00; A01N 55/00; A01N 43/80; A01N 61/00; A01N 41/10; A01N 47/36; A01N 33/18; A01N 43/10; A01N 43/50; A01N 43/58; A01N 47/12; A01N 47/30; A01N 57/28; A01N 35/06; A01N 43/82; A01N 25/18
See application file for complete search history.

(56) References Cited

U.S. PATENT DOCUMENTS

| | | | | |
|---|---|---|---|---|
| 8,071,116 B2 * | 12/2011 | Sirinyan | ................ | A01N 43/56 424/405 |
| 9,137,995 B2 * | 9/2015 | Sirinyan | ................ | A01N 43/56 |
| 2010/0016398 A1 * | 1/2010 | Sirinyan | ................ | A01N 43/56 514/407 |

* cited by examiner

*Primary Examiner* — Audrea Buckley
(74) *Attorney, Agent, or Firm* — McBee Moore Woodward & Vanik IP, LLC

(57) ABSTRACT

The invention relates to novel compositions for controlling parasites on animals, comprising an N-arylpyrazole and also a pyrethroid in a formulation comprising aliphatic cyclic carbonates and aliphatic cyclic or acyclic polyethers.

13 Claims, No Drawings

COMBINATION PRODUCT FOR CONTROLLING PARASITES ON ANIMALS

The invention relates to novel compositions for controlling parasites on animals, comprising an N-arylpyrazole and also a pyrethroid in a formulation comprising aliphatic cyclic carbonates and aliphatic cyclic or acyclic polyethers.

N-Arylpyrazoles and their good insecticidal and acaricidal activity are known from US 2006014802 A1, WO2005090313 A1, FR2834288 A1, WO09828277, U.S. Pat. No. 6,069,157, WO200031043, DE19824487, WO09804530, WO09962903, EP00933363, EP00911329, WO09856767, U.S. Pat. No. 5,814,652, WO09845274, WO9840359, WO09828279, WO09828278, DE19650197, WO09824767, EP00846686, EP00839809, WO09728126, EP00780378, GB02308365, U.S. Pat. No. 5,629,335, WO09639389, U.S. Pat. No. 5,556,873, EP00659745, U.S. Pat. No. 5,321,040, EP00511845, EP-A-234119, EP-A-295117 and WO 98/24769. In spite of this abundance of applications with numerous N-arylpyrazole structures, there is a superior structure type which, for most indications, shows, by comparison, the best activity. 1-[2,6-Dichloro-4-(trifluoromethyl)phenyl]-3-cyano-4-[(trifluoromethyl)-sulphinyl]-5-aminopyrazole (INN: fipronil) is generally acknowledged to be the most effective compound of this class for controlling most parasites.

N-Arylpyrazoles have been marketed as ectoparasiticides for more than 10 years (Hunter, J. S., III, D. M. Keister and P. Jeannin. 1994. Fipronil: A new compound for animal health. Proc. Amer. Assoc. Vet. Parasitol. 39th Ann. Mtg. San Francisco, Calif. Pg. 48). They are distinguished by good and broad activity and acceptable compatibility. It is known that the existing formulations having a high content of DEE (Transcutol) contain a strong transdermal (FR 1996-11446 A; Sicherheitsdatenblatt [Safety data sheet]: ISO/DIS 11014/29 CFR 1910.1200/ANSI Z400.1 Printing date Oct. 23, 2001: FRONTLINE® TOP SPOT™: fipronil 9.7% w/w) component. This facilitates, via the formulation, penetration into the sebaceous glands and the epithelium (Skin distribution of fipronil by microautoradiography following topical administration to the beagle dog. Cochet, Pascal; Birckel, P.; Bromet-Petit, M.: Bromet, N.: Weil, A.; European Journal of Drug Metabolism and Pharmacokinetics (1997), 22(3), 211-216). Via sebum excretion from the sebaceous glands, a high concentration in the sebaceous glands may contribute to a long-lasting availability of the active compound if the active compound is carried along. However, in the case of the customary formulations, penetration of N-arylpyrazoles into the circulation is also likely, since each hair follicle is supplied by a blood vessel and the follicles are thus separated from the circulation only by a very thin barrier (Transfollicular drug delivery—Is it a reality? Meidan, Victor M.; Bonner, Michael C.; Michniak, Bozena B.; International Journal of Pharmaceutics (2005), 306(1-2), 1-14). Thus, the availability of the active compound on the animal is limited, too, both with respect to duration and concentration, since the active compound passes into the circulation and its available concentration in the sebum is lowered accordingly.

It is further known that the efficacy of the N-arylpyrazoles against representatives of the genus *Ixodes* is less than that against other genera of ticks (Endris R G, Matthewson, Cooke D & Amodie D (2000). Rellency and efficacy of 65% permethrin and 9.7% fipronil against *Ixodes ricinus*. Vet. Therapeutics, Vol. 1 (No, 3): 159-168); Endris R G, Cooke D, Amodie D, Sweenwy D L & Katz T L (2002). Repellency and efficacy of 65% permethrin and selamectin spot-on formulations against *Ixodes ricinus* on dogs. Vet. Therapeutics. Vol. 3 (No. 1): 64-71).

Pyrethroids do likewise have a relatively broad insecticidal action, and some representatives also show good acaricidal effects; however, with these compounds there are frequently incompatibilities, and only particularly non-toxic representatives with limited efficacy can be used for cats. Recently, WO 04/098290 described a solution of this problem where a dosage tolerated by cats could be achieved with the aid of a synergist, an acaricidal pyrethroid and a neonicotinoid. The different physicochemical properties of the materials used require special formulations.

Furthermore, it is generally known that, compared to N-arylpyrazoles, pyrethroids are less active against ticks of the genus *Dermacentor*. Recently, it has furthermore been found that there is no cross-resistance between pyrethroids and N-arylpyrazoles in pyrethroid-resistant insects. On the other hand, selection of such mosquito strains with N-arylpyrazoles even leads to partial reversion of the pyrethroid resistance.

[Laboratory evaluation of fipronil, a phenylpyrazole insecticide, against adult *Anopheles* (Diptera: Culicidae) and investigation of its possible cross-resistance with dieldrin in *Anopheles stephensi*. Kolaczinski, Jan; Curtis, Chris. London School of Hygiene and Tropical Medicine, London, UK. Pest Management Science (2001), 57(1), 41-45].

WO 2001/065941 A1 and EP 1013170 A1 propose the combination of an N-arylpyrazole and a pyrethroid in applications against plant pests. JP 11049618 A2 uses similar mixtures to prevent feeding damage on timber constructions. WO 95/22902 A1 uses such mixtures for the direct control of termites. FR 2713891 A1 and WO 95/22902 A1 even claim a synergistic effect of such mixtures, but without demonstrating it clearly.

However, [Antagonism of fipronil toxicity by piperonyl butoxide and 5,5,5-tributyl phosphorotrithioate in the German cockroach (Dictyoptera: Blattellidae). Valles, Steven M.; Koehler, Philip G.; Brenner, Richard J. Center for Medical, Agricultural and Veterinary Entomology, USDA-ARS, Gainesville, Fla., USA. Journal of Economic Entomology (1997), 90(5), 1254-1258] indicates that inhibitors of the oxidative metabolism (P450 oxidase inhibitors) have an antagonistic effect in cockroaches on the action of N-arylpyrazoles. Since most pyrethroids are detoxified via the p450 oxidase path, they, like MGK264 or piperonyl butoxide, have to be considered to be antagonists rather than synergists of the N-arylpyrazoles.

GB2396557 A1 teaches that the treatment of ectoparasites with mixtures of N-arylpyrazoles and pyrethroids (if appropriate also with addition of synergists, such as MGK264 or piperonyl butoxide) is possible when concentrated powder formulations are used. WO 95/22902 A1 describes a soil treatment with improved activity by combined application of phenylpyrazoles and pyrethroids for control of termites. Here, too, the mixture used is unsuitable for application on homeotherms.

Since such formulations are difficult to apply in practice and, owing to the particles (GB 2396557), involve additional toxicological risks, it has to be the object to prepare a self-spreading liquid formulation having a good user safety profile which combines the positive activity properties of the pyrethroids with those of the N-arylpyrazoles and does not result in a reduction of the efficacy of the N-arylpyrazoles even in the presence of further synergists from the class of the p450 oxidase inhibitors.

To this end, by intensive analyses and test series, we have now identified, from a large number of additives, solvents and spreading agents, formulations which, in general, can improve the good arthropodicidal efficacy properties of the N-arylpyrazoles in combination with pyrethroids. Surprisingly, the expected antagonistic effects were not observed here.

The invention relates to novel compositions for controlling parasites on animals, comprising an N-arylpyrazole and a pyrethroid in a formulation comprising:
an aliphatic cyclic carbonate
an aliphatic cyclic or acyclic polyether.

The arthropodicidal compositions according to the invention are novel and, compared to the formulations hitherto described, have considerably better and longer-lasting efficacy, with simultaneously improved user and target animal safety profile.

For the compositions, the combination partners of the N-arylpyrazoles are preferably arthropodicidal pyrethroids, in particular of the cyanopyrethroid (for example flumethrin), type-1 pyrethroid (for example permethrin) or non-ester pyrethroid (etofenprox) type.

Here, α-cyanopyrethroids (for example alpha-cypermethrin, cyfluthrin, beta-cyfluthrin, cyhalothrin, cypermethrin, deltamethrin, fenvalerate, flucythrinate, flumethrin, tau-fluvalinate) are preferably employed in a concentration range of from 0.01 to 5% by weight, and a synergist is added, if appropriate (as described, for example, in WO 04/098290). Particular preference is given to using cypermethrin, cyfluthrin, deltamethrin and flumethrin in a concentration range of from 0.025 to 0.25% by weight. Very particular preference is given to using flumethrin in a concentration range of from 0.05 to 1.25% by weight.

Type-1 pyrethroids (for example allethrin, bioallethrin, permethrin, phenothrin, resmethrin, tetramethrin, transfluthrin) are preferably employed in a concentration range of from 20 to 70% by weight. Particular preference is given here to permethrin, cyphenothrin in a concentration range of from 30 to 60% by weight. Very particular preference is given to using permethrin in concentrations of from 40 to 50% by weight.

Non-ester pyrethroids (for example etofenprox, halfenprox, silafluofen) are usually employed in a concentration range of from 10 to 60% by weight. Preference is given to etofenprox or halfenprox; particular preference is given to etofenprox in a concentration range of 25-55%.

To the person skilled in the art, N-arylpyrazoles are known per se as arthropodicidally active compounds, for example from the documents mentioned above, which are incorporated herein by way of reference.

Preferred phenylpyrazoles are those of the formula (I):

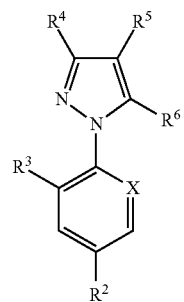

(I)

in which
X represents =N— or C—$R^1$,
$R^1$ and $R^3$ independently of one another represent halogen,
$R^2$ represents halogen, $C_{1-3}$-haloalkyl, $S(O)_nCF_3$ or $SF_5$,
n represents 0, 1 or 2,
$R^4$ represents hydrogen, cyano or a radical of the formula

or one of the cyclic substituents below:

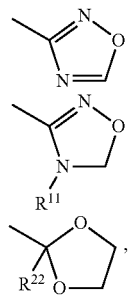

$R^5$ represents hydrogen, $C_{2-4}$-alkynyl, $C_{2-4}$-alkenyl which may optionally be mono- or polysubstituted by halogen or $C_{1-3}$-alkyl, or $R^5$ represents $C_{1-4}$-alkyl-(C=O)—, $C_{1-4}$-alkyl-S—, $C_{1-4}$-haloalkyl-S—, —S(=O)—$C_{1-4}$-alkyl or —S(=NH)—$C_{1-4}$-alkyl, optionally halogen-substituted phenyl, optionally halogen-substituted furyl, the radical —$NR^{14}R^{15}$, an oxiranyl radical which is optionally mono- or polysubstituted by $C_{1-4}$-alkyl or $C_{1-4}$-haloalkyl, or a cyclopropyl radical which is optionally mono- or polysubstituted by halogen, $C_{1-4}$-alkyl or $C_{1-4}$-haloalkyl,
$R^6$ represents hydrogen, $C_{1-4}$-alkylcarbonyl or a radical —$NR^{16}R^{17}$,
$R^7$ represents hydrogen, $C_{1-4}$-alkyl, $C_{1-4}$-alkyl-S— or —$NR^9R^{10}$,
Y represents =S, =O, =NH, =N—$C_{1-4}$-alkyl, =N—OH or

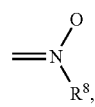

$R^8$ represents $C_{1-4}$-alkyl,
$R^9$ and $R^{10}$ independently of one another represent hydrogen, hydroxyl or $C_{1-4}$-alkyl,
$R^{11}$ represents hydrogen, $C_{1-4}$-alkyl, —COO—$C_{1-4}$-alkyl or —$CONR^{12}R^{13}$,
$R^{12}$ and $R^{13}$ independently of one another represent hydrogen or $C_{1-4}$-alkyl,
$R^{14}$ and $R^{15}$ independently of one another represent hydrogen, $C_{1-4}$-alkyl, $C_{1-4}$-haloalkyl or $C_{1-4}$-alkyl-$SO_2$—,
$R^{16}$ and $R^{17}$ independently of one another represent hydrogen, $C_{1-4}$-alkoxy or $C_{1-4}$-alkyl, where the $C_{1-4}$-alkyl may optionally be substituted by phenyl, pyranzinyl or pyridyl, where phenyl, pyranzinyl or pyridyl may be mono- or polysubstituted by hydroxyl, $C_{1-4}$-alkyl, $C_{1-4}$-haloalkyl and/or $C_{1-4}$-alkoxy, or $R^{16}$ and $R^{17}$ represent $C_{1-4}$-alkylcarbonyl, $C_{1-4}$-alkoxycarbonyl, $C_{1-4}$-alkoxy-$C_{1-4}$-alkylcarbonyl or the radical —(C=O)NR$^{20}$R$^{21}$ or $R^{16}$ and $R^{17}$ together represent the group =CR$^{18}$R$^{19}$ which is attached by a double bond to the nitrogen, $R^{18}$ and $R^{19}$ independently of one another represent phenyl which is optionally mono- or polysubstituted by hydroxyl, $C_{1-4}$-alkyl, $C_{1-4}$-haloalkyl and/or $C_{1-4}$-alkoxy, and/or $R^{18}$ and $R^{19}$ represent hydrogen, $C_{1-4}$-alkyl, $C_{1-4}$-alkenyl or $C_{1-4}$-alkoxy, where $C_{1-4}$-alkyl, $C_{1-4}$-alkenyl or $C_{1-4}$-alkoxy may optionally be substituted by phenyl which is optionally mono- or polysubstituted by hydroxyl, $C_{1-4}$-alkyl, $C_{1-4}$-haloalkyl and/or $C_{1-4}$-alkoxy, $R^{20}$ and $R^{21}$ independently of one another represent hydrogen, $C_{1-4}$-alkyl or phenyl which is optionally mono- or polysubstituted by hydroxyl, $C_{1-4}$-alkyl, $C_{1-4}$-haloalkyl and/or $C_{1-4}$-alkoxy, $R^{22}$ represents $C_{1-4}$-alkyl.

Halogen preferably represents fluorine, chlorine, bromine or iodine, in particular fluorine, chlorine or bromine.

$C_{1-4}$-Alkyl represents straight-chain or branched alkyl having 1 to 4 carbon atoms, such as, for example, methyl, ethyl, n-propyl, isopropyl, n-butyl, sec-butyl, tert-butyl.

$C_{1-4}$-Haloalkyl represents straight-chain or branched alkyl having 1 to 4 carbon atoms which is substituted by one or more identical or different halogen atoms; this also includes perhaloalkyl compounds. Preference is given to fluoroalkyls. Examples are —CF$_2$H, —CF$_3$, —CH$_2$CF$_3$, —CF$_2$CF$_3$.

Preferably, the substituents have the following meanings:

X preferably represents C—R$^1$.

$R^1$ and $R^3$ independently of one another preferably represent chlorine or bromine.

$R^2$ preferably represents $C_{1-3}$-haloalkyl or SF$_5$.

$R^4$ preferably represents hydrogen, cyano or a radical of the formula

or one of the cyclic substituents below:

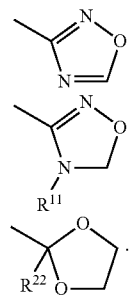

$R^5$ preferably represents hydrogen, $C_{2-3}$-alkynyl, $C_{2-3}$-alkenyl which may optionally be monosubstituted by halogen or $C_{1-3}$-alkyl, or $R^5$ preferably represents $C_{1-3}$-alkyl-(C=O)—, $C_{1-3}$-alkyl-S—, $C_{1-3}$-haloalkyl-S—, —S(=O)—$C_{1-3}$-alkyl or —S(=NH)—$C_{1-3}$-alkyl, optionally halogen-substituted phenyl, optionally halogen-substituted furyl, the radical —NR$^{14}$R$^{15}$, an optionally $C_{1-3}$-haloalkyl-substituted oxiranyl radical or a cyclopropyl radical which is optionally mono- or polysubstituted by halogen, $C_{1-4}$-alkyl or $C_{1-4}$-haloalkyl.

$R^6$ preferably represents hydrogen, $C_{1-3}$-alkylcarbonyl or a radical —NR$^{16}$R$^{17}$.

$R^7$ preferably represents hydrogen, $C_{1-4}$-alkyl, $C_{1-4}$-alkyl-S— or —NR$^9$R$^{10}$.

Y preferably represents =S, =O, =NH, =N—OH or

$R^8$ preferably represents $C_{1-3}$-alkyl.

$R^9$ and $R^{10}$ independently of one another preferably represent hydrogen, hydroxyl or $C_{1-3}$-alkyl.

$R^{11}$ preferably represents hydrogen, $C_{1-4}$-alkyl or —CONR$^{12}$R$^{13}$.

$R^{12}$ and $R^{13}$ independently of one another preferably represent hydrogen or $C_{1-3}$-alkyl.

$R^{14}$ and $R^{15}$ independently of one another preferably represent hydrogen, $C_{1-3}$-alkyl, $C_{1-3}$-haloalkyl or $C_{1-3}$-alkyl-SO$_2$—.

$R^{16}$ and $R^{17}$ independently of one another preferably represent hydrogen, $C_{1-3}$-alkoxy or $C_{1-3}$-alkyl, where the $C_{1-3}$-alkyl may optionally be substituted by phenyl, pyrazinyl or pyridyl, where phenyl, pyrazinyl or pyridyl may be mono- or disubstituted by hydroxyl, $C_{1-3}$-alkyl, $C_{1-3}$-haloalkyl and/or $C_{1-3}$-alkoxy, or $R^{16}$ and $R^{17}$ represent $C_{1-4}$-alkylcarbonyl, $C_{1-4}$-alkoxycarbonyl, $C_{1-4}$-alkoxy-$C_{1-4}$-alkylcarbonyl or the radical —(C=O)NR$^{20}$R$^{21}$ or $R^{16}$ and $R^{17}$ together represent the group =CR$^{18}$R$^{19}$ which is attached by a double bond to the nitrogen.

$R^{18}$ and $R^{19}$ independently of one another preferably represent phenyl which is optionally mono- or disubstituted by hydroxyl, $C_{1-3}$-alkyl, $C_{1-3}$-haloalkyl and/or $C_{1-3}$-alkoxy, and/or $R^{18}$ and $R^{19}$ represent hydrogen, $C_{1-3}$-alkyl, $C_{1-3}$-alkenyl or $C_{1-3}$-alkoxy, where $C_{1-3}$-alkyl, $C_{1-3}$-alkenyl or $C_{1-3}$-alkoxy may optionally be substituted by phenyl which is optionally mono- or disubstituted by hydroxyl, $C_{1-4}$-alkyl, $C_{1-4}$-haloalkyl and/or $C_{1-4}$-alkoxy.

$R^{20}$ and $R^{21}$ independently of one another preferably represent $C_{1-3}$-alkyl or phenyl which is optionally mono- or disubstituted by hydroxyl, $C_{1-3}$-alkyl, $C_{1-3}$-haloalkyl and/or $C_{1-3}$-alkoxy.

$R^{22}$ preferably represents $C_{1-3}$-alkyl.

Particularly preferably, the substituents in formula (I) have the meaning below:

X represents C—R$^1$.

$R^1$ and $R^3$ each represent Cl.

$R^2$ represents CF$_3$.

$R^4$ represents CN, —C(=S)NH$_2$ or —C(=O)CH$_3$.

$R^5$ represents —SCHF$_2$, —S(=O)CF$_3$, —S(=O)CH$_3$, —S(=O)CH$_2$CH$_3$ or represents the 1-trifluoromethyloxiranyl radical.

$R^6$ represents an amino group or one of the radicals below

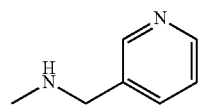

-continued
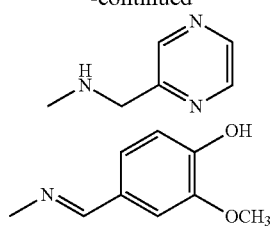
Preferred examples of compounds which can be used according to the invention are listed below:
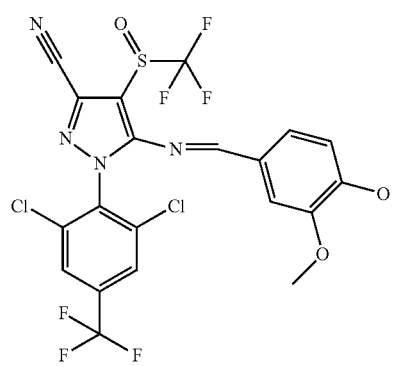
EP00511845
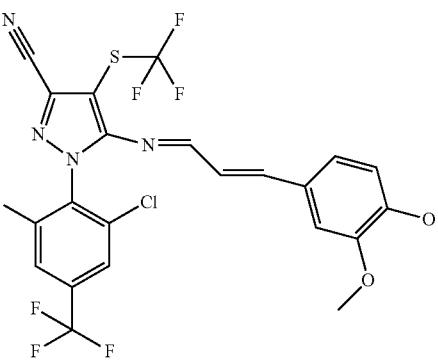
U.S. Pat. No. 5,321,040
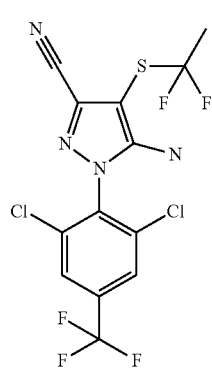
EP00659745
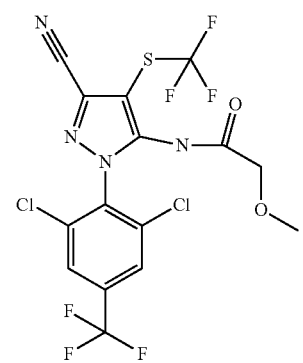
U.S. Pat. No. 5,556,873
-continued
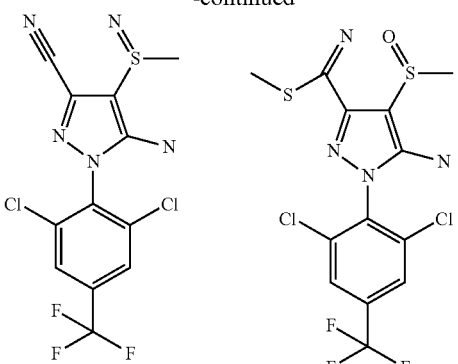
Salt with 2,4,6-trimethyl-
benzenesulphonic acid
WO09639389
U.S. Pat. No. 5,629,335
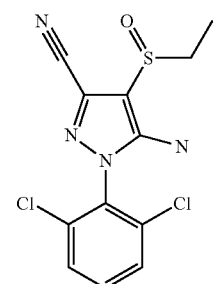
GB02308365
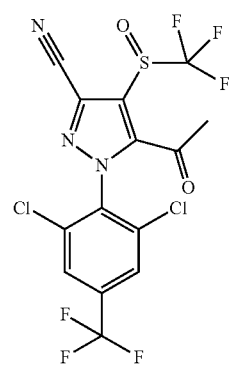
EP00780378
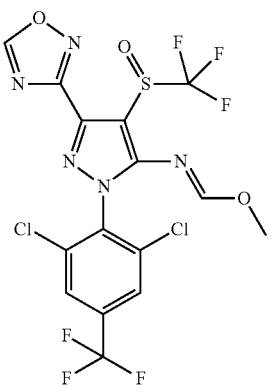
WO09728126
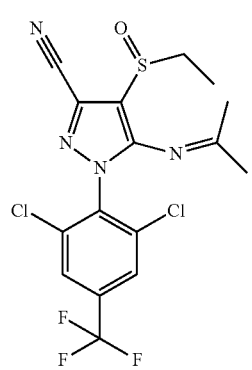
EP00839809
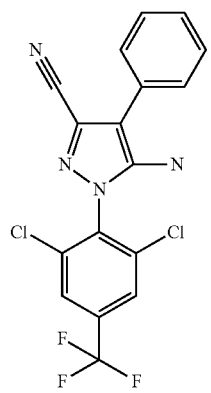
EP00846686
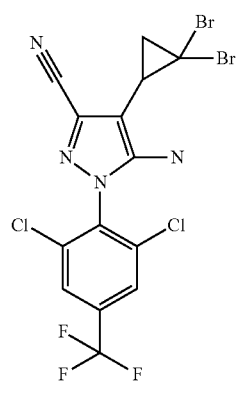
WO09824767

-continued
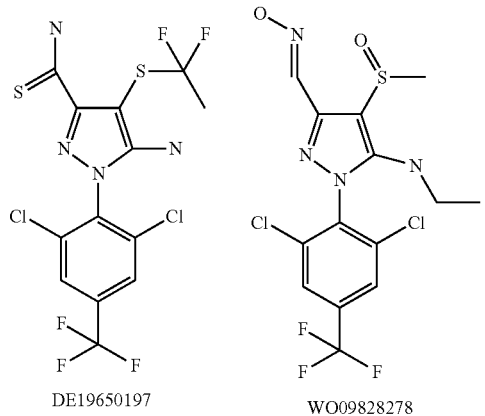
DE19650197　　WO09828278
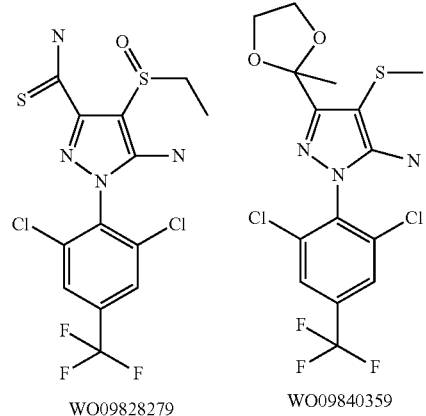
WO09828279　　WO09840359
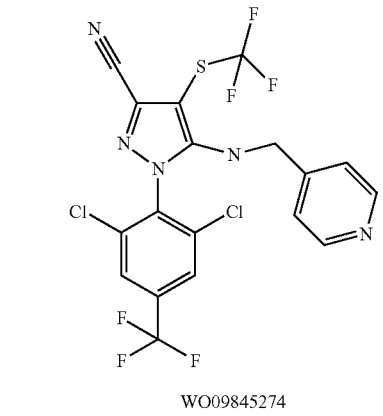
WO09845274
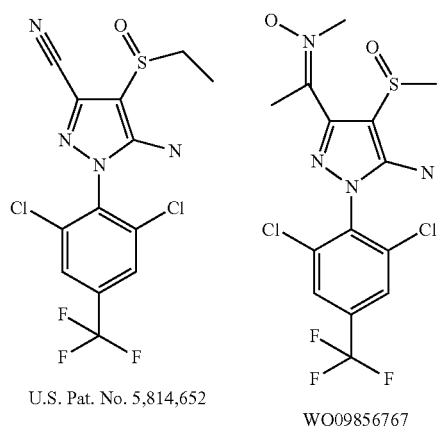
U.S. Pat. No. 5,814,652　　WO09856767
-continued
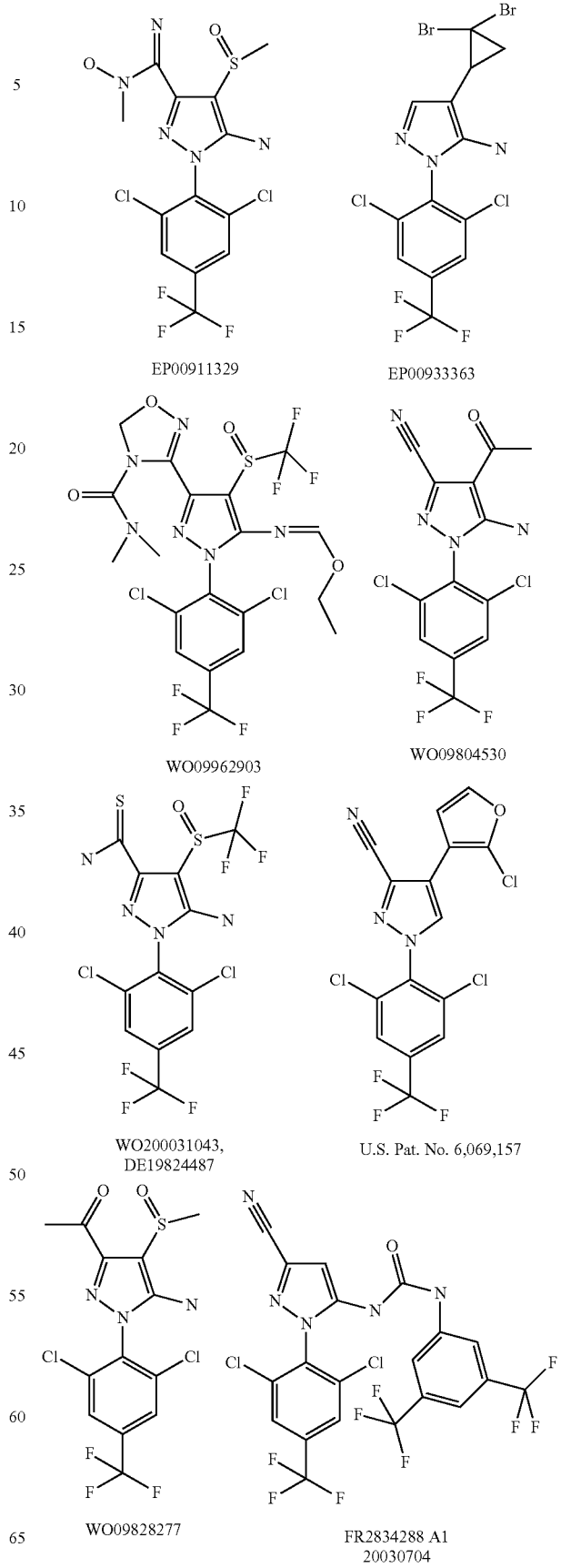
EP00911329　　EP00933363
WO09962903　　WO09804530
WO200031043,
DE19824487　　U.S. Pat. No. 6,069,157
WO09828277　　FR2834288 A1
20030704

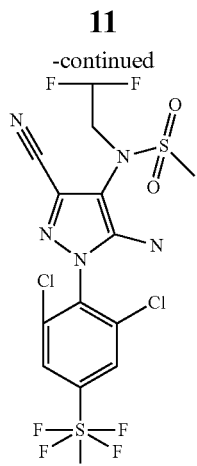

WO2005090313 A1
20050929

Particularly preferred examples of compounds which can be used according to the invention are:

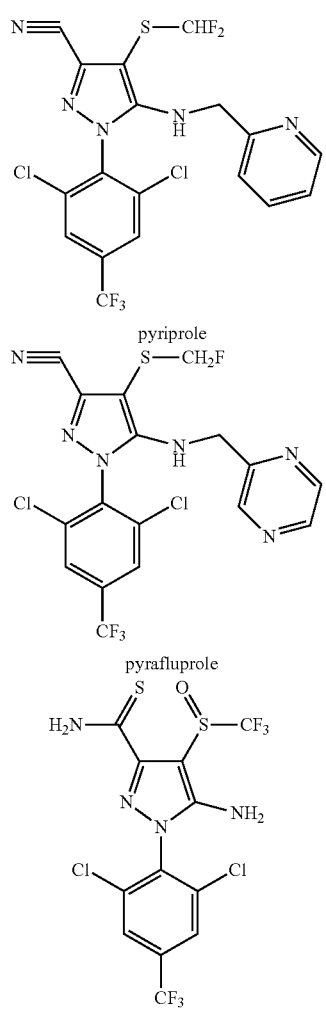

pyriprole pyrafluprole 5-amino-4-trifluoromethyl-
sulphinyl-1-(2,6-dichloro-4-
trifluoromethylphenyl)-3-
thiocarbamoylpyrazole

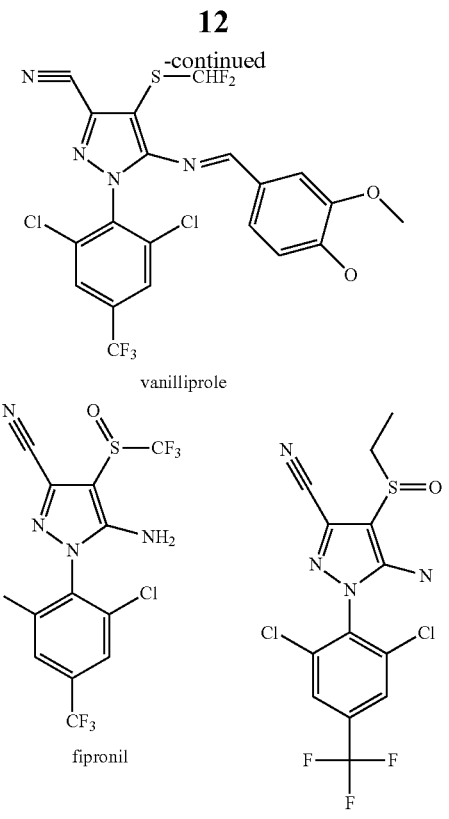

vanilliprole fipronil ethiprole

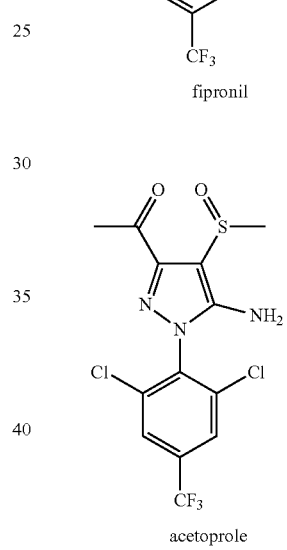

acetoprole

JP08311036,
Takeda

An example of a very particularly preferred N-arylpyrazole is fipronil.

A further example of a very particularly preferred N-arylpyrazole is 5-amino-4-trifluoromethylsulphinyl-1-(2,6-dichloro-4-trifluoromethylphenyl)-3-thio-carbamoylpyrazole.

Depending on the nature and arrangement of the substituents, the active compounds may, if appropriate, be present in various stereoisomeric forms, in particular as enantiomers and racemates. According to the invention, it is possible to use both the pure stereoisomers and mixtures thereof.

If appropriate, the active compounds can also be employed in the form of their salts, pharmaceutically acceptable acid addition salts and basic salts being suitable.

Suitable pharmaceutically acceptable salts are salts of mineral acids or organic acids (for example carboxylic acids or sulphonic acids). Examples which may be mentioned are salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. Suitable pharmaceutically acceptable basic salts are, for example, the alkali metal salts, for example the sodium or potassium salts, and the alkaline earth metal salts, for example the magnesium or calcium salts.

It is furthermore also possible to use the active compounds in the form of their solvates, in particular hydrates. Solvates are to be understood as meaning both the solvates, in particular hydrates, of the active compounds themselves and the solvates, in particular hydrates, of their salts.

As solids, the active compounds may, in certain cases, form various crystal modifications. Advantageous for the use in medicaments are stable modifications having suitable solubility properties.

Unless indicated otherwise, percentages are to be understood as percent by weight based on the weight of the finished preparation.

Usually, the compositions comprise the arylpyrazole in amounts of from 1 to 27.5% by weight, preferably from 5 to 20% by weight, particularly preferably from 7.5 to 15% by weight.

The aliphatic cyclic carbonate is preferably ethylene carbonate or propylene carbonate, it also being possible to use mixtures.

The amount of aliphatic cyclic carbonate in the formulation can be varied widely in the range of from 10% by weight to 70% by weight, preferably from 12.5 to 50% by weight, particularly preferably from 15 to 40% by weight.

Aliphatic cyclic and/or acyclic ethers are compounds known per se. Preferably, they are ethers derived from diols having up to 8 carbon atoms, such as, for example, ethylene glycol, diethylene glycol, propylene glycol, dipropylene glycol. In the acyclic ethers, one or both OH groups carry a $C_{1-4}$-alkyl group, preferably, only one OH group is etherified; particularly preferred examples are: diethylene glycol monoethyl ether, diethylene glycol monopropyl ether, dipropylene glycol monopropyl ether. Preferred 5- or 6-membered cyclic ethers have a ring oxygen and 4 or 5 ring carbon atoms and optionally carry a $C_{1-4}$-alkyl substituent; preferably, they carry a free OH group either directly on the ring or on the $C_{1-4}$-alkyl substituent. A particularly preferred example is tetrahydrofurfuryl alcohol. The amount of aliphatic, cyclic and/or acyclic ether in the compositions according to the invention can be varied within wide limits of from 20 to 77.5% by weight, with amounts in the range of from 25 to 65% by weight and amounts in the range of from 25 to 50% by weight being particularly preferred and very particularly preferred, respectively.

According to a preferred embodiment, the compositions according to the invention may additionally comprise one or more esters of a dihydric or trihydric alcohol having up to three carbon atoms with organic fatty acids having 6 to 18 carbon atoms. As alcohol component, the esters used according to the invention contain a di- or trihydric alcohol having up to three carbon atoms, such as, for example, ethylene glycol, propylene glycol or glycerol. In general, at least two, preferably all, hydroxyl groups of the alcohol are esterified. The acid components of the esters are fatty acids having 6 to 18 carbon atoms, which may be straight-chain, branched and also mono- or polyunsaturated. It is possible to use mixed esters or else mixtures of various types of esters. Preferred triglycerides are caprylic/capric acid triglycerides and also caprylic/capric/linoleic acid triglycerides. Preference is likewise given to esters of propylene glycol with caprylic and/or capric acid (propylene glycol octanoate decanoate). Particularly preferably, these glycerol or propylene glycol esters of caprylic/capric acid have a viscosity range (20° C.) of 0.08-1.3 Pa·s, and preferably 0.08-0.40 Pa·s. It is also possible to use their polyethylene oxide-, polypropylene oxide- and/or propylene carbonate-modified derivatives having the viscosity range mentioned. Examples which may be mentioned are propylene glycol dicaprylate, propylene glycol octanoate decanoate having a viscosity range of 0.09-0.12 Pa·s, caprylic/capric diglyceryl succinate having a mean viscosity of 0.23 Pa·s, medium-chain caprylic/capric triglycerides having a viscosity of 0.27-0.30 Pa·s.

The liquid formulations according to the invention may comprise one or more of the esters mentioned above. Usually, the compositions according to the invention comprise the ester or the ester mixture in proportions of from 0 to 40% by weight, preferably from 1 to 35% by weight, particularly preferably from 1 to 12.5% by weight and very particularly preferably from 2.5 to 7.5% by weight.

If appropriate, customary organic or inorganic antioxidants may be used for stabilizing the formulations mentioned. Suitable inorganic antioxidants are, for example, the sulphites and bisulphites, in particular sodium bisulphite. Preference is given to phenolic antioxidants, such as anisole, butylated hydroxytoluene and hydroxyanisole, and their mixtures with one another. Usually, from 0.01 to 1% by weight, preferably from 0.05% to 0.5%, particularly preferably from 0.075 to 0.2% by weight is used.

The formulation ingredients mentioned, in particular the organic esters, may be stabilized against possible hydrolytic degradation using acidifying agents. Suitable acidifying agents are pharmaceutically acceptable acids, in particular carboxylic acids, such as, for example, succinic acid, tartaric acid, lactic acid or citric acid. Their preferred amount is in the range of from 0 to 0.5% by weight, but preferably from 0 to 0.2% by weight.

Polymeric surfactants based on polymethoxysiloxanes having a low surface tension of <30 mN/m, preferably <22 mN/m, can be used as further formulation auxiliaries for improving the spreadability. Such surfactants are known ethoxylated and/or propoxylated, preferably neutral or particularly preferably cationic formulation auxiliaries. An example of a preferred polymeric auxiliary which may be mentioned is the methoxysilane/ethylene oxide copolymer Belisil Silvet L 77 from Bayer GE Siliconics GmbH. The amount of these formulation auxiliaries may be varied within wide limits in the range of from 0.01 to 1.0% by weight. The preferred range is from 0.2 to 0.4% by weight.

If appropriate, the formulations may comprise further pharmaceutically acceptable auxiliaries and additives.

In addition to the arylpyrazoles and pyrethroids, the compositions according to the invention may also comprise one or more additional active compounds. Preferred examples of such active compounds for combinations which may be mentioned are: growth inhibitors, such as, for example, chitin biosynthesis inhibitors, such as, for example, benzoylphenylureas (for example triflumuron, lufenuron); phenyloxazolines (for example etoxazole); juvenile hormone analogues (for example methoprene, hydroprene, pyriproxifen) and also mixtures of these active compounds with one another. Their amount may be varied within wide limits in the range of from 0.1 to 7.5% by weight, but preferably from 0.25 to 5.0% by weight, particularly preferably from 0.25 to 2.5% by weight.

The formulations according to the invention may also comprise synergists. Synergists in the sense of this application are to be understood as meaning compounds which for their part do not have the desired activity, but which, as mixing partners, increase the activity of the active compounds. Piperonyl butoxide, MGK264, verbutin, S,S,S-tributyl phosphorotrithioate may be mentioned here in an exemplary manner. In the formulations according to the invention, synergists are preferably used for α-cyanopyrethroids, namely in a synergist:pyrethroid ratio of 20-50:1 (see also WO 04/098290). The preferred synergist is MGK264.

The compositions according to the invention are environmentally compatible and have a low toxicity which is reduced compared to that of known compositions. Accordingly, they are user-friendly and furthermore distinguished by their easy handling. The compositions have a favourable flashpoint of >70° C. and can therefore be manufactured in simple plants which do not require additional measures to protect against explosions.

Having favourable homeotherm toxicity, the compositions of the invention are suitable for controlling parasitic arthropods, in particular insects and arachnids, very particularly fleas and ticks, encountered on animals, in particular homeotherms, particularly preferably mammals. These animals may be domestic animals and useful animals and also zoo animals, laboratory animals, test animals and pets.

The compositions described herein are used in particular against ectoparasites on pets, in particular dogs and cats, and useful animals.

The compositions of the invention are active against all or individual stages of development of the pests and against resistant and normally sensitive pest species.

The pests include:
from the order of the Anoplura, for example, *Haematopinus* spp., *Linognathus* spp., *Solenopotes* spp., *Pediculus* spp., *Pthirus* spp.;
from the order of the Mallophaga, for example, *Trimenopon* spp., *Menopon* spp., *Eomenacanthus* spp., *Menacanthus* spp., *Trichodectes* spp., *Felicola* spp., *Damalinea* spp., *Bovicola* spp;
from the order of the Diptera, suborder Brachycera, for example, *Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmeromyia* spp., *Cordylobia* spp., *Cochliomyia* spp., *Chrysomyia* spp., *Sarcophaga* spp., *Wohlfartia* spp., *Gasterophilus* spp., *Oesteromyia* spp., *Oedemagena* spp., *Hypoderma* spp., *Oestrus* spp., *Rhinoestrus* spp., *Melophagus* spp., *Hippobosca* spp.
from the order of the Diptera, suborder Nematocera, for example, *Culex* spp., *Aedes* spp., *Anopheles* spp., *Culicoides* spp., *Phlebotomus* spp., *Simulium* spp.
from the order of the Siphonaptera, for example, *Ctenocephalides* spp., *Echidnophaga* spp., *Ceratophyllus* spp., *Pulex* spp.
from the order of the Metastigmata, for example, *Hyalomma* spp., *Rhipicephalus* spp., *Boophilus* spp., *Amblyomma* spp., *Haemaphysalis* spp., *Dermacentor* spp., *Ixodes* spp., *Argas* spp., *Ornithodorus* spp., *Otobius* spp.;
from the order of the Mesostigmata, for example, *Dermanyssus* spp., *Ornithonyssus* spp., *Pneumonyssus* spp.
from the order of the Prostigmata, for example, *Cheyletiella* spp., *Psorergates* spp., *Myobia* spp., *Demodex* spp., *Neotrombicula* spp.;
from the order of the Astigmata, for example, *Acarus* spp., *Myocoptes* spp., *Psoroptes* spp., *Chorioptes* spp., *Otodectes* spp., *Sarcoptes* spp., *Notoedres* spp., *Knemidocoptes* spp., *Neoknemidocoptes* spp., *Cytodites* spp., *Laminosioptes* spp.

Particular emphasis may be given to the action against fleas (Siphonaptera, for example, *Ctenocephalides* spp., *Echidnophaga* spp., *Ceratophyllus* spp., *Pulex* spp.), ticks (*Hyalomma* spp., *Rhipicephalus* spp., *Boophilus* spp., *Amblyomma* spp., *Haemaphysalis* spp., *Dermacentor* spp., *Ixodes* spp., *Argas* spp., *Ornithodorus* spp., *Otobius* spp.) and the Diptera mentioned above (*Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmeromyia* spp., *Cordylobia* spp., *Cochliomyia* spp., *Chrysomyia* spp., *Sarcophaga* spp., *Wohlfartia* spp., *Gasterophilus* spp., *Oesteromyia* spp., *Oedemagena* spp., *Hypoderma* spp., *Oestrus* spp., *Rhinoestrus* spp., *Melophagus* spp., *Hippobosca* spp.).

The useful and breeding animals include mammals, such as, for example, cattle, horses, sheep, pigs, goats, camels, water buffalo, donkeys, rabbits, fallow deer, reindeer, fur-bearing animals, such as, for example, mink, chinchilla, raccoon, birds, such as, for example, hens, geese, turkeys, ducks.

The laboratory animals and test animals include mice, rats, guinea pigs, rabbits, golden hamsters, dogs and cats.

The pets include dogs and cats.

Particular emphasis is given to application on cat and dog.

Application can take place both prophylactically and therapeutically.

Preferably, the liquid formulations according to the invention are suitable for spot-on, pour-on or spray application, where the spray application may be carried out, for example, using a pump spray or an aerosol spray (pressurized spray). For specific indications, the formulations may also be used after dilution with water as a dip; in this case, the formulation should contain emulsifying additives.

The preferred application forms are pump spray, pour-on and spot-on. The spot-on application is very particularly preferred.

The formulations according to the invention are distinguished by their excellent compatibility with customary "single-dose" plastic tubes and by their storage stability in various climate zones. They have low viscosity and can be applied without any problems.

The liquid formulations according to the invention can be prepared by mixing appropriate amounts of the components with one another, using, for example, conventional stirring tanks or other suitable instruments. If required by the ingredients, it is also possible to operate under a protective atmosphere or with other methods of excluding oxygen.

EXAMPLES

Example 1

100 ml of liquid formulation consisting of 10.0 g of 5-amino-4-trifluoromethylsulphinyl-1-(2,6-dichloro-4-trifluoromethyl-phenyl)-3-thiocarbamoylpyrazole 57.30 g of diethylene glycol monoethyl ether 0.10 g of BHT 0.20 g of BHA 30.02 g of propylene carbonate 5.00 g of propylene glycol octanoate decanoate 0.24 g of flumethrin 10.36 g of MGK 264

0.02 g of citric acid

Example 2

100 ml of liquid formulation consisting of
10.00 g of 5-amino-4-trifluoromethylsulphinyl-1-(2,6-dichloro-4-trifluoromethyl-phenyl)-3-thiocarbamoylpyrazole
0.24 g of flumethrin
0.02 g of citric acid
0.20 g of BHT
68.00 g of dipropylene glycol monomethyl ether
13.40 g of propylene carbonate
5.00 g of demineralized water
5.00 g of propylene glycol octanoate decanoate
5.00 g of MGK 264

Example 3

100 ml of liquid formulation consisting of
10.00 g of 5-amino-4-trifluoromethylsulphinyl-1-(2,6-dichloro-4-trifluoromethyl-phenyl)-3-thiocarbamoylpyrazole
0.50 g of PPF (pyriproxyfen)
0.24 g of flumethrin
0.02 g of citric acid
0.20 g of BHT
67.50 g of dipropylene glycol monomethyl ether
13.40 g of propylene carbonate
5.00 g of demineralized water
5.00 g of propylene glycol octanoate decanoate
5.00 g of MGK 264

Example 4

100 ml of liquid formulation consisting of
10.00 g of 5-amino-4-trifluoromethylsulphinyl-1-(2,6-dichloro-4-trifluoromethyl-phenyl)-3-thiocarbamoylpyrazole
0.50 g of PPF (pyriproxyfen)
0.24 g of flumethrin
0.02 g of citric acid
0.20 g of BHT
60.90 g of diethylene glycol monoethyl ether
20.00 g of propylene carbonate
5.00 g of demineralized water
5.00 g of propylene glycol octanoate decanoate
5.00 g of MGK 264

Example 5

100 ml of liquid formulation consisting of
10.00 g of 5-amino-4-trifluoromethylsulphinyl-1-(2,6-dichloro-4-trifluoromethyl-phenyl)-3-thiocarbamoylpyrazole
45.00 g of permethrin
37.90 g of diethylene glycol monoethyl ether
0.10 g of BHT
0.20 g of BHA
25.00 g of propylene carbonate
5.00 g of propylene glycol octanoate decanoate
0.02 g of citric acid

Example 6

100 ml of liquid formulation consisting of
10.00 g of 5-amino-4-trifluoromethylsulphinyl-1-(2,6-dichloro-4-trifluoromethyl-phenyl)-3-thiocarbamoylpyrazole
45.00 g of permethrin
1.00 g of PPF
36.90 g of diethylene glycol monoethyl ether
0.10 g of BHT
0.20 g of BHA
25.00 g of propylene carbonate
5.00 g of propylene glycol octanoate decanoate
0.02 g of citric acid

Example 7

100 ml of liquid formulation consisting of
10.00 g of 5-amino-4-trifluoromethylsulphinyl-1-(2,6-dichloro-4-trifluoromethyl-phenyl)-3-thiocarbamoylpyrazole
45.00 g of permethrin
1.00 g of PPF
0.25 g of Silvet L 77 from GE Siliconocs GmbH D-51368 Leverkusen
36.65 g of diethylene glycol monoethyl ether
0.10 g of BHT
0.20 g of BHA
25.00 g of propylene carbonate
5.00 g of propylene glycol octanoate decanoate
0.02 g of citric acid

Example 8

10.00 g of 5-amino-4-trifluoromethylsulphinyl-1-(2,6-dichloro-4-trifluoromethyl-phenyl)-3-thiocarbamoylpyrazole
45.00 g of permethrin
1.00 g of PPF
0.25 g of Silvet L 77 (from Bayer-GE Silicones GmbH, D-51368 Leverkusen)
36.65 g of diethylene glycol monoethyl ether
0.10 g of BHT
0.20 g of BHA
25.00 g of ethylene carbonate
5.00 g of propylene glycol octanoate decanoate
0.02 g of citric acid

Comparative Example 1

A commercially available 10% fipronil spot-on formulation from Merial Ltd., 3239 Satellite Blvd., Duluth, Ga. 30096-4640, USA.

Comparative Example 2

A formulation comprising 5-amino-4-trifluoromethylsulphinyl-1-(2,6-dichloro-4-trifluoromethylphenyl)-3-thiocarbamoylpyrazole, but without added flumethrin or MGK264:
100 ml of liquid formulation consisting of
10.00 g of 5-amino-4-trifluoromethylsulphinyl-1-(2,6-dichloro-4-trifluoromethyl-phenyl)-3-thiocarbamoylpyrazole
57.7 g of diethylene glycol monoethyl ether
40.0 g of propylene carbonate
5.0 g of propylene glycol octanoate decanoate
0.1 g of butylated hydroxytoluene
0.2 g of butylated hydroxyanisole

Comparative Example 3

A formulation comprising flumethrin and MGK264 and PPF, but, instead of the 3-thiocarbamoylpyrazole mentioned in the application, the known insecticide imidacloprid.

100 ml of liquid formulation consisting of
10.00 g of imidacloprid
0.50 g of PPF
56.80 g of benzyl alcohol
0.10 g of BHT
0.20 g of BHA
30.02 g of propylene carbonate
5.00 g of propylene glycol octanoate decanoate
0.24 g of flumethrin
10.36 g of MGK 264
0.02 g of citric acid Biological Examples All compounds were metered out exactly by weight to ensure better comparability. To this end, 20 pipettes of the fipronil-containing commercial preparation were emptied into a glass bottle and likewise blinded using a code.

All samples were applied as a single spot to the neck (cats and smaller dogs) using Eppendorf pipettes (volume up to 0.95 ml). For application volumes of more than 1 ml, the volume was halved and applied to the neck as two spots at a distance of about 10 cm.

Further laboratory tests for the activity against fleas and ticks according to Example 2 show that the preparations in the abovementioned formulations according to the invention have very good and long-lasting action against ticks and fleas which, in the tests, is consistently superior to the prior art (CE1-CE3). Furthermore, the preparations in the abovementioned formulations according to the invention are distinguished in that they are tolerated by target animal and user, and they are thus highly suitable for controlling fleas and ticks on small animals.

A. Activity Against Fleas (*Ctenocephalides felis*) on Dogs

Between days −4 and −1, dogs are infested 1-2 times with about 100 adult unfed *Ctenocephalides felis* per dog. The fleas are placed on the neck of the animal. On day 0, the success of the infestation on the dog is examined by checking the awake animal for fleas. The number of live fleas is noted.

After the fleas have been counted, the animals are treated. The dogs of the control group are not treated. The medicaments to be examined are administered to the animals dermally as a spot-on in an application rate of 0.1-0.15 ml/kg of bodyweight or as a spray in an application rate of 1-1.5 ml/kg of bodyweight. The application is carried out once on day 0. Only animals that are clinically healthy are used.

On days 1 and 2, all dogs are examined for live fleas. The results are noted with the crude data.

On days 7, 14, 21, 28 and 35 and, if appropriate, also on days 42 and 49, all dogs are reinfested with about 100 adult unfed *Ctenocephalides felis* per dog. In each case one day after the reinfestation, all dogs are checked for live fleas. The results are noted with the crude data.

A formulation is considered to be highly effective if, between 24 and 48 hours after reinfestation, an efficacy of >95% is found, and this action persists for at least 3-4 weeks.

The efficacy is calculated using a modified formula according to Abbott:

$$\text{Efficacy \%} = \frac{\text{number of fleas } CG - \text{number of fleas } TG}{\text{number of fleas } CG} \times 100$$

CG: control group; TG: treatment group

The medicaments of Formulation Example 2, applied as a spot-on at a dosage of 0.15 ml/kg, were found to be highly effective against *Ctenocephalides felis*.

B. Activity Against Ticks (*Rhipicephalus sanguineus, Dermacentor variabilis*) on Dogs Between days −4 and −1, dogs are sedated using 2% Rompun® (Bayer AG, active compound: xylazine hydrochloride) (0.1 ml/kg of bodyweight). Once all dogs have been sedated (after about 10-15 minutes), they are transferred to transport boxes, and 50 *Rhipicephalus sanguineus* or *Dermacentor variabilis* (25♀, 25♂) per dog are applied to the neck of the animal. After about 1½ hours, the animals are retransferred from the transport box into the cage.

On day 0, the success of the infestation on the dog is examined by checking the awake animal for ticks. An intensive search is carried out in the region of the head and the ears, including the folds of the ears, in the region of the neck, on the lower abdomen, on the lower breast, on the flank and in between the toes and on the limbs. The number of sucking live ticks is noted. Dead ticks are removed.

After the ticks have been counted, the animals are treated. The dogs of the control group are not treated. The medicaments to be examined are administered to the animals dermally as a spot-on at 0.1-0.15 ml/kg of bodyweight or as a spray at 1-1.5 ml/kg of bodyweight. The application is carried out once on day 0. Only animals which are clinically healthy are used.

On day 1 and day 2, all dogs are checked for living and dead sucking ticks. The results are noted with the crude data. On day 2, all living and dead ticks are removed from the dog.

On days 7, 14, 21, 28, 35 and, if appropriate, also on days 42 and 49, all dogs are reinfested with in each case 50 *Rhipicephalus sanguineus* or *Dermacentor variabilis* (25♀, 25♂) per dog. In each case two days after the reinfestation, all dogs are checked for living and dead sucking ticks. The results are noted with the crude data. On the second day after the reinfestation, all living and dead ticks are removed from the dog.

A formulation is considered to be highly effective if, on day 2 and in each case on the second day after reinfestation, an efficacy of >90% is found, and this action persists for at least 3 weeks.

For calculating the efficacy, a modified formula according to Abbott is used:

$$\text{Efficacy \%} = \frac{\text{number of ticks } CG - \text{number of ticks } TG}{\text{number of ticks } CG} \times 100$$

CG: control group; TG: treatment group

The medicaments according to Formulation Example 2, applied as a spot-on at a dosage of 0.15 ml/kg, were found to be highly effective against *Rhipicephalus sanguineus*.

C. Activity Against Fleas (*Ctenocephalides felis*) on Cats

On day −1, cats are infested with about 100 adult unfed *Ctenocephalides felis* per cat. The fleas are placed on the neck of the animal.

On day 0, the success of the infestation on the cat is examined by checking the awake animal for fleas. The number of live fleas is noted.

After the fleas have been counted, the animals are treated. The cats of the control group are not treated. The medicaments to be examined are administered to the animals dermally as a spot-on in an application rate of 0.1-0.15 ml/kg of bodyweight. The application is carried out once on day 0. Only animals that are clinically healthy are used.

On day 2, all cats are examined for live fleas. The results are noted with the crude data.

On days 7, 14, 21, 28 and 35 and, if appropriate, also on days 42 and 49, all cats are reinfested with about 100 adult unfed *Ctenocephalides felis* per cat. In each case two days after reinfestation, all cats are checked for live fleas. The results are noted with the crude data.

A formulation is considered to be highly effective if, on day 2 and in each case on the second day after reinfestation, an efficacy of >95% is found, and this action persists for at least 3-4 weeks.

The efficacy is calculated using a modified formula according to Abbott:

$$\text{Efficacy \%} = \frac{\text{number of fleas } CG - \text{number of fleas } TG}{\text{number of fleas } CG} \times 100$$

CG: control group; TG: treatment group

The medicaments of Formulation Example 2, applied as a spot-on at a dosage of 0.15 ml/kg, were found to be highly effective against *Ctenocephalides felis*.

D. Activity Against Ticks (*Ixodes ricinus*) on Cats

In each case on day −2, cats are sedated using a mild sedative (acepromazine maleate). Once all cats have been sedated (after about 10-15 minutes), 30-50 *Ixodes ricinus* (15-25♀, 15-25♂) per cat are applied to the neck of the animal.

On day −1, the success of the infestation on the cats is examined by checking the awake animal for ticks. An intensive search is carried out in the region of the head and the ears, in the region of the neck, on the lower abdomen, on the lower breast, on the flank and on the limbs. The number of sucking live ticks is noted. Dead ticks are removed.

After the ticks have been counted, the animals are divided into groups. Treatment is carried out on day 0. The cats of the control group are not treated. The medicaments to be examined are administered to the animals dermally, as a spot-on at 0.1-0.15 ml/kg of bodyweight. Application is carried out once on day 0. Only animals which are clinically healthy are used.

On day 2, all cats are checked for living and dead sucking ticks. The results are noted with the crude data. All living and dead ticks are removed from the cat. On days 7, 14, 21, 28 and 35 and, if appropriate, also on days 42 and 49, all cats are reinfested with in each case 30-50 *Ixodes ricinus* (15-25♀, 15-25♂) per cat. In each case two days after the reinfestation, all cats are checked for living and dead sucking ticks. The results are noted with the crude data. On the second day after the reinfestation, all living and dead ticks are removed from the cat.

A formulation is considered to be highly effective if, on day 2 and in each case on the second day after reinfestation, an efficacy of >90% is found, and this action persists for at least 3 weeks.

For calculating the efficacy, a modified formula according to Abbott is used:

$$\text{Efficacy \%} = \frac{\text{number of ticks } CG - \text{number of ticks } TG}{\text{number of ticks } CG} \times 100$$

CG: control group; TG: treatment group

The medicaments according to Formulation Example 2, applied as a spot-on at a dosage of 0.15 ml/kg, were found to be highly effective against *Ixodes ricinus*.

E. Efficacy Against Fleas and Ticks Over 4 to 7 Weeks

The efficacy of the compositions according to the invention against fleas and ticks was tested over a period of four to seven weeks. The test was carried out according to the description under items A to D.

TABLE 1a

Efficacy of the composition according to Example 2 against fleas on cats

| 10 Treatment | Appl. Vol ml/kg | Parasite | W0 D2 | | WD D9 | | W2 D16 | | W3 D23 | | W4 D30 | | W5 D37 |
|---|---|---|---|---|---|---|---|---|---|---|---|---|---|
| 1. infestation day-4 | CE 1 | 0.1 | *Ctenocephalides felis* | 97 | 2. infestation day 7 | 100 | 3. infestation day 14 | 100 | 4. infestation day 21 | 100 | 5. infestation day 28 | 99 | 6. Infestation day 35 | 100 |
| | CE 2 | 0.15 | *Ctenocephalides felis* | 99 | | 100 | | 100 | | 100 | | 100 | | 99 |
| | Example 2 | 0.15 | *Ctenocephalides felis* | 99 | | 100 | | 100 | | 100 | | 100 | | 100 |
| | CE 3 | 0.1 | *Ctenocephalides felis* | 100 | | 100 | | 100 | | 99 | | 94 | | 74 |

TABLE 1b

Efficacy of the composition according to Example 2 against ticks on cats

| 10 Treatment | Appl. Vol ml/kg | Parasite | W0 D2 | | WD D9 | | W2 D16 | | W3 D23 | | W4 D30 | | W5 D37 |
|---|---|---|---|---|---|---|---|---|---|---|---|---|---|
| 1. infestation day-4 | CE 1 | 0.1 | *Ixodes ricinus* | 74 | 2. infestation day 7 | 99 | 3. infestation day 14 | 96 | 4. infestation day 21 | 72 | 5. infestation day 28 | 82 | 6. Infestation day 35 | 89 |
| | CE 2 | 0.15 | *Ixodes ricinus* | 84 | | 99 | | 92 | | 84 | | 73 | | 68 |
| | Example 2 | 0.15 | *Ixodes ricinus* | 70 | | 100 | | 100 | | 97 | | 100 | | 95 |

TABLE 1b-continued

Efficacy of the composition according to Example 2 against ticks on cats

| Treatment | Appl. Vol ml/kg | Parasite | W0 D2 | WD D9 | W2 D16 | W3 D23 | W4 D30 | W5 D37 |
|---|---|---|---|---|---|---|---|---|
| CE 3 | 0.1 | Ixodes ricinus | 71 | 100 | 100 | 96 | 93 | 76 |

Appl. Vol = volume applied in ml/kg of bodyweight
"value" % = efficacy in %, calculated via determination of the geometrical mean compared to an untreated control group TABLE 2a Efficacy of the composition according to Example 2 against fleas on dogs

| D0 Treatment | Appl. Vol ml/kg | Parasite | W0 D2 | W1 D9 | W2 D16 | W3 D23 | W4 D30 | W5 D37 | W6 D44 | W7 D51 |
|---|---|---|---|---|---|---|---|---|---|---|
| 1. infestation day-4 | CE 1 | 0.1 | Ctenocephalides felis | 100 | 100 | 100 | 99 | 99 | 100 | 62 | 33 |
| | CE 2 | 0.15 | Ctenocephalides felis | 100 | 100 | 100 | 100 | 100 | 99 | 99 | 76 |
| 2. infestation day-1 | Example 2 | 0.15 | Ctenocephalides felis | 100 | 99 | 100 | 100 | 100 | 100 | 100 | 77 |
| | CE 3 | 0.1 | Ctenocephalides felis | 100 | 100 | 100 | 100 | 98 | 74 | nd | nd |

Reinfestations: 3. infestation day 7; 4. infestation day 14; 5. infestation day 21; 6. infestation day 28; 7. Infestation day 35; 8. infestation day 42; 9. infestation day 49

TABLE 2b

Efficacy of the composition according to Example 2 against ticks on dogs

| D0 Treatment | Appl. Vol ml/kg | Parasite | W0 D2 | W1 D9 | W2 D16 | W3 D23 | W4 D30 | W5 D37 | W6 D44 | W7 D51 |
|---|---|---|---|---|---|---|---|---|---|---|
| 1. infestation day-4 | CE 1 | 0.1 | Rhipicephalus sanguineus | 97 | 100 | 100 | 100 | 99 | 94 | 93 | 65 |
| | CE 2 | 0.15 | Rhipicephalus sanguineus | 96 | 100 | 100 | 100 | 100 | 99 | 98 | 74 |
| 2. infestation day-1 | Example 2 | 0.15 | Rhipicephalus sanguineus | 92 | 100 | 100 | 100 | 100 | 99 | 99 | 88 |
| | CE 3 | 0.1 | Rhipicephalus sanguineus | 60 | 94 | 99 | 98 | 98 | 91 | nd | nd |

Reinfestations: 3. infestation day 7; 4. infestation day 14; 5. infestation day 21; 6. infestation day 28; 7. Infestation day 35; 8. infestation day 42; 9. infestation day 49

Appl. Vol = volume applied in ml/kg of bodyweight
"value" % = efficacy in %, calculated via determination of the arithmetic mean compared to an untreated control group

TABLE 3

Efficacy of the composition according to Example 2 against ticks on dogs

| D0 Treatment | Appl. Vol ml/kg | Parasite | W0 D2 | W1 D9 | W2 D16 | W3 D23 | W4 D30 |
|---|---|---|---|---|---|---|---|
| 1. infestation day-4 | CE 1 | 0.15 | Dermacentor variabilis | 25 | 98 | 99 | 100 | 98 |
| | Example 2 | 0.15 | Dermacentor variabilis | 55 | 100 | 99 | 100 | 100 |
| | CE 3 | 0.1 | Dermacentor variabilis | 34 | 89 | 80 | 66 | 87 |

Reinfestations: 2. infestation day 7; 3. infestation day 14; 4. infestation day 21; 5. infestation day 28

Appl. Vol = volume applied in ml/kg of bodyweight
"value" % = efficacy in %, calculated via determination of the geometrical mean compared to an untreated control group

The invention claimed is:

1. A composition for controlling parasites on animals, comprising:
   a. fipronil;
   b. phenothrin;
   c. an aliphatic cyclic carbonate; and
   d. an aliphatic cyclic or acyclic polyether.

2. The composition of claim 1, further comprising an ester of a dihydric or trihydric alcohol having up to three carbon atoms with organic fatty acids having 6 to 18 carbon atoms.

3. The composition of claim 1, wherein the fipronil is present in an amount of from 1 to 27.5% by weight of the composition.

4. The composition of claim 1, wherein the aliphatic cyclic carbonate is present in an amount of from 10 to 70% by weight of the composition.

5. The composition of claim 1, wherein the aliphatic cyclic or acyclic polyether is present in an amount of from 20 to 77.5% by weight of the composition.

6. The composition of claim 1, wherein the fipronil is present in an amount of from 7.5 to 15% by weight of the composition.

7. The composition of claim 1, wherein the cyclic carbonate is selected from the group consisting of ethylene carbonate, propylene carbonate, and mixtures thereof.

8. The composition of claim 1, wherein the aliphatic cyclic carbonate is present in an amount of from 15 to 40% by weight of the composition.

9. The composition of claim 1, wherein the aliphatic cyclic or acyclic polyether is selected from the group consisting of diethylene glycolmonoethyl ether, diethylene glycol monopropyl ether, dipropylene glycol monopropyl ether, and tetrahydrofurfuryl alcohol.

10. A composition for controlling ticks on dogs, comprising:
    a. fipronil;
    b. phenothrin;
    c. propylene carbonate; and
    d. dipropylene glycol monomethyl ether.

11. A method of controlling ticks on an animal, which comprises applying to said animal an effective amount of the composition of claim 10.

12. The composition of claim 1, wherein the phenothrin is present in an amount of from 20 to 70% by weight of the composition.

13. The composition of claim 10, wherein the phenothrin is present in an amount of from 20 to 70% by weight of the composition.

* * * * *